(12) United States Patent
Kim et al.

(10) Patent No.: US 12,194,189 B2
(45) Date of Patent: Jan. 14, 2025

(54) STABLE COMPOSITIONS COMPOSED OF A RADIOPAQUE AGENT AND CYANOACRYLATE MONOMER AND APPLICATIONS THEREOF

(71) Applicant: Chemence Medical, Inc., Alpharetta, GA (US)

(72) Inventors: David Kim, Marietta, GA (US); Laura Bassam, Woodstock, GA (US); Stephen Hynes, Atlanta, GA (US); Kenneth Broadley, Alpharetta, GA (US)

(73) Assignee: CHEMENCE MEDICAL, INC., Alpharetta, GA (US)

( * ) Notice: Subject to any disclaimer, the term of this patent is extended or adjusted under 35 U.S.C. 154(b) by 802 days.

(21) Appl. No.: 17/274,927

(22) PCT Filed: Sep. 9, 2019

(86) PCT No.: PCT/US2019/050200
§ 371 (c)(1),
(2) Date: Mar. 10, 2021

(87) PCT Pub. No.: WO2020/060786
PCT Pub. Date: Mar. 26, 2020

(65) Prior Publication Data
US 2022/0031907 A1 Feb. 3, 2022

Related U.S. Application Data

(60) Provisional application No. 62/732,060, filed on Sep. 17, 2018.

(51) Int. Cl.
*A61L 24/00* (2006.01)
*A61K 6/30* (2020.01)
*A61L 24/06* (2006.01)

(52) U.S. Cl.
CPC .............. *A61L 24/001* (2013.01); *A61K 6/30* (2020.01); *A61L 24/06* (2013.01);
(Continued)

(58) Field of Classification Search
CPC ......... A61K 6/30; A61L 24/001; A61L 24/06; A61L 2300/202; A61L 2300/802; A61L 2430/36
See application file for complete search history.

(56) References Cited

U.S. PATENT DOCUMENTS 4,783,484 A 11/1988 Violante et al.
5,318,767 A 6/1994 Liversidge et al.
(Continued)

FOREIGN PATENT DOCUMENTS

EP 0050457 A1 4/1982
WO WO-2005006991 A2 * 1/2005 ............. A61F 6/225

OTHER PUBLICATIONS

Petrie, "Cyanoacrylate Adhesives in Surgical Applications: A Critical Review" in Rev. Adhesion Adhesives, vol. 2, No. 3, Aug. 2014. (Year: 2014).*
(Continued)

*Primary Examiner* — Blessing M Fubara
(74) *Attorney, Agent, or Firm* — Thomas | Horstemeyer, LLP (57) ABSTRACT

Described herein are compositions composed of a radiopaque agent and a cyanoacrylate monomer. These compositions cure in situ when administered to a subject and, thus, have numerous biomedical applications. The presence of the radiopaque agent allows the practitioner to visualize the compositions during and immediately after administration to the subject. The compositions are non-toxic and shelf-stable, and can be sterilized to prevent microbial growth. The compositions can be pre-mixed prior (Continued)

to sale and distribution, reducing the need for special training in their use.

37 Claims, 2 Drawing Sheets

(52) U.S. Cl.
CPC ............... *A61L 2300/202* (2013.01); *A61L 2300/802* (2013.01); *A61L 2430/36* (2013.01)

(56) References Cited

U.S. PATENT DOCUMENTS

| | | | |
|---|---|---|---|
| 5,521,218 A | 5/1996 | Osifo | |
| 5,776,496 A | 7/1998 | Violante et al. | |
| 5,846,515 A | 12/1998 | Krishnan et al. | |
| 6,599,448 B1 | 7/2003 | Ehrhard, Jr. et al. | |
| 7,166,570 B2 | 1/2007 | Hunter et al. | |
| 2002/0055573 A1* | 5/2002 | Malofsky | A61P 17/04 524/418 |
| 2005/0149173 A1 | 7/2005 | Hunter et al. | |
| 2007/0208134 A1 | 9/2007 | Benjamin | |
| 2008/0009902 A1 | 1/2008 | Hunter et al. | |
| 2008/0200586 A1 | 8/2008 | Holden et al. | |
| 2010/0074934 A1 | 3/2010 | Hunter | |
| 2011/0052503 A1* | 3/2011 | Almen | A61K 49/0438 424/9.4 |

OTHER PUBLICATIONS

Supplementary European Search Report for EP Application No. 19861639 mailed May 12, 2022.

Halliwell, Lauren, Investigation and synthesis of alkyl cyanoacrylates and modification of X-ray contrast agents for incorporation into alkyl cyanoacrylate for use in medical devices, Mar. 2013, University of Warwick, Department of Chemistry, United Kingdom. http://go.warwick.ac.uk/wrap.

International Search Report and Written Opinion for PCT/US19/50200 mailed Nov. 27, 2019.

Petrie et al. 'Cyanoacrylate Adhesives in Surgical Applications: A Critical Review', Rev. Adhesion Adhesives, 2014, vol. 2, No. 3, pp. 253-310. abstract; p. 276, para 4; p. 299, Table 20; p. 298, Table 19; p. 254, para 2; p. 276, para 3-4; p. 296, para 4; p. 300, para 5; p. 301, para 1.

* cited by examiner

STABLE COMPOSITIONS COMPOSED OF A RADIOPAQUE AGENT AND CYANOACRYLATE MONOMER AND APPLICATIONS THEREOF

CROSS REFERENCE TO RELATED APPLICATIONS

This application claims priority upon U.S. provisional application Ser. No. 62/732,060, filed Sep. 17, 2018. This application is hereby incorporated by reference in its entirety.

BACKGROUND

Numerous radiopaque agents are known in the art. Many of these agents are iodinated organic compounds, where iodine's high electron density causes it to readily appear in X-ray images and are stable in the body and rapidly eliminated. Ionic iodinated contrast media include diatrizoate (HYPAQUE 50®), metrizoate (CORONAR 370®), and ioxaglate (HEXABRIX®), while nonionic iodinated contrast media include iopamidol (ISOVUE-370®), iohexol (OMNIPAQUE 350®), and iodixanol (VISIPAQUE 320®). These may variously exhibit high or low osmolality relative to blood, plasma, and cerebrospinal fluid, and may be sold in monomeric or dimeric form.

The treatment of arteriovenous malformations with butyl cyanoacrylate combined with iodinated ethyl esters of poppy seed oil is known in the art. These cyanoacrylate embolic agents may also contain tantalum powder as an image contrast booster. However, the iodinated esters destabilize the butyl cyanoacrylate and thus these treatments are not shelf-stable and their components must be mixed immediately prior to use. Careful mixing is required to achieve the required viscosity and cure speed before injection, which requires significant skill. These commercial products are thus difficult to use and necessitate a good deal of training for new surgeons.

Other commercially available radiopaque agents are generally not stable or soluble in n-butyl cyanoacrylate, or exhibit improved stability but low solubility limits that preclude their use as radiopaque agents. What is needed are compositions composed of a radiopaque agent that exhibit a shelf life of at least several months and up to a year when mixed with a cyanoacrylate.

SUMMARY

Described herein are compositions composed of a radiopaque agent and a cyanoacrylate monomer. These compositions cure in situ when administered to a subject and, thus, have numerous biomedical applications. The presence of the radiopaque agent allows the practitioner to visualize the compositions during and immediately after administration to the subject. The compositions are non-toxic and shelf-stable, and can be sterilized to prevent microbial growth. The compositions can be pre-mixed prior to sale and distribution, reducing the need for special training in their use.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Before the present materials, articles, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and appended claims, the singular forms "a," "an," and "the" include plural referents unless the context clearly dictates otherwise. Thus, for example, reference to "a radiopaque agent" includes mixtures of two or more radiopaque agents, and the like.

"Optional" or "optionally" means that the subsequently described event or circumstance can or cannot occur, and that the description includes instances where the event or circumstance occurs and instances where it does not. For example, the pharmaceutical compositions described herein may optionally contain one or more viscosity modifiers, where the viscosity modifiers may or may not be present.

As used herein, the term "about" is used to provide flexibility to a numerical range endpoint by providing that a given value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

A "subject" as used in the specification and concluding claims refers to a human or non-human animal. For example, the subject can be a non-human animal (domesticated, wild, or farm) such as, for example, a horse, cat, dog, cow, pig, sheep, goat, mouse, rabbit, chicken, rat, or guinea pig.

"Physiological conditions" as used herein refers to parameters such as pH, temperature, etc., within a subject. For example, the physiological pH and temperature of a human are 7.2 and 37° C., respectively.

The term "admixing" is defined as mixing two components together so that there is no chemical reaction or physical interaction. The term "admixing" also includes the chemical reaction or physical interaction between the two components.

As an example, non-covalent entrapment of a radiopaque agent in a cured cyanoacrylate matrix is possible.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl, and the like. Examples of longer chain alkyl groups include, but are not limited to, a palmitate group. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorus.

As used herein, an "allyl group" consists of a methylene bridge (—$CH_2$—) attached to a vinyl group (—CH=$CR^3_2$) where each $R^3$ can be the same or different, and can independently be a hydrogen, alkyl, cycloalkyl, or aryl group. Examples of allyl groups include, but are not limited to, methylallyl, dimethylallyl, ethylallyl, diethylallyl, phenylallyl, methylphenylallyl, ethylphenylallyl, butylallyl, propylallyl, and the like.

The term "aryl" group as used herein is any carbon-based aromatic group including, but not limited to, benzene, naphthalene, etc. The term "aryl group" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. In one aspect, the heteroaryl group is imidazole. The aryl group can be substituted or unsubstituted. The aryl group can be substituted with one or more groups including, but not limited to, alkyl, alkynyl, aryl, halide, nitro, amino, ester, ketone, aldehyde, hydroxy, carboxylic acid, or alkoxy.

As used herein, an "aralkyl" group is any group derived from an alkyl group by replacing one or more hydrogen atoms of the alkyl group with an aryl group. Aralkyl groups include, but are not limited to, benzyl groups and other groups formed by substituting an aryl group for a hydrogen atom in an alkyl group as defined above.

The term "carboxyl group" refers to carboxylic acids and esters thereof. Non-limiting examples of carboxylic acids include formic acid, acetic acid, propionic acid, butyric acid, valeric acid, caproic acid, enanthic acid, caprylic acid, pelargonic acid, capric acid, lauric acid, myristic acid, palmitic acid, stearic acid, arachidic acid, palmitoleic acid, oleic acid, linoleic acid, linolenic acid, arachidonic acid, glyoxylic acid, glycolic acid, acrylic acid, propiolic acid, malonic acid, tartronic acid, mesoxalic acid, dihydroxymalonic acid, lactic acid, hydracrylic acid, glyceric acid, glycidic acid, isobutyric acid, acetoacetic acid, fumaric acid, maleic acid, oxaloacetic acid, tartric acid, crotonic acid, adipic acid, citric acid, aconitic acid, isocitric acid, sorbic acid, benzoic acid, salicylic acid, and the like. Esters of carboxylic acids can be any alkyl, cycloalkyl, allyl, or aralkyl ester. In some instances, carboxyl groups include acid anhydrides.

As used herein, a "carboxyalkyl group" is a group or substituent having both an alkyl group and a carboxy group. Carboxyalkyl groups include, but are not limited to, esters of lactic acid and hydroxy hexanoate as well as esters of any of the carboxyl groups already listed.

An "iodo-substituted" group as used herein is any alkyl, cycloalkyl, aryl, allyl, aralkyl, or carboxyalkyl group containing an iodine atom in the place of one or more hydrogen atoms. Iodo-substituted groups include, but are not limited to, iodobenzyl groups and/or iodo-substituted alkyl groups. In some aspects, the procedure for modifying a compound to include iodine is known in the art. In a further aspect, including iodine as a substituent on another chemical component leads to radiopacity and facilitates visual examination via X-ray or similar imaging.

"Embolus" as used herein refers to a mass capable of blocking a blood vessel to seal blood cells and plasma inside the vessel or to prevent the flow of blood through a vessel. In one aspect, the compositions disclosed herein can form emboli at the site of application or injection.

A "tumor," as used herein, is a non-specific term for a mass or neoplasm (i.e., abnormal growth of cells in a subject), which may be benign or malignant (i.e., cancerous). In one aspect, a tumor may have an extensive blood supply and the compositions disclosed herein can be injected into vessels surrounding the tumor in order to cut off blood supply to the tumor.

An "aneurysm" occurs when an artery wall weakens, which can lead to abnormal widening of the artery or even rupture. In one aspect, the compositions disclosed herein can be applied at or near the site of an aneurysm to strengthen the artery wall, to plug or seal a rupture, or to cut off blood flow to the area surrounding the aneurysm.

A "varicose vein" as used herein is an enlarged vein, often in the legs or feet, that can become tortuous or gnarled. Varicose veins may occur or worsen due to improper closing or function of valves in the veins, impeding or reducing the effectiveness of blood flow, including allowing blood to pool in the veins. In one aspect, the compositions disclosed herein can be injected into or near varicose veins to form emboli, cutting off blood flow to the veins.

As used herein, an "arteriovenous malformation" is a defect in the blood vessels, often, but not exclusively, associated with the brain or spinal cord. An arteriovenous malformation or AVM is an abnormal grouping of blood vessels connecting arteries and veins that can disrupt normal blood flow and, hence, oxygen circulation. The presence of an AVM can lead to inadequate oxygenation of tissues as well as weakening and rupture of the arteries and/or veins. In one aspect, the compositions disclosed herein can be used to treat an AVM such as, for example, by strengthening weakened blood vessel walls or by embolizing improperly formed vessels.

A "wound" is an injury to living tissue. Formation of a wound typically involves cutting or breaking the skin, either accidentally or deliberately (i.e., from a medical procedure). A wound may be caused by a cut, burn, chemical exposure, blow, fall, or impact, or may result from a skin condition or bacterial infection. A wound may also be internal. In one aspect, the compositions disclosed herein can be used to seal minor wounds or surgical incisions or to stop blood flow from an internal wound or from a wound on the surface of the body.

As used herein, "fracture" refers to a break in bone or cartilage, which may be caused by an injury or a disease or hereditary condition. In one aspect, the compositions disclosed herein can be applied to the sites of fractures to help set the bone and maintain it in position during healing.

A "fistula" is a passage between a hollow or tubular organ and the body surface, or between two hollow or tubular organs. A fistula may be surgically created or can be the result of an injury or congenital defect. In one aspect, the compositions disclosed herein can be used to fill in fistulas to prevent transfer of the contents of one organ to another or to the outside of the body, to reduce the likelihood of infection, or as scaffolding to promote correction of the fistula.

"Adhesion" refers to the union of two opposing tissue surfaces. Adhesion can be desirable, as with the closing of a wound or surgical incision, and in this instance, the compositions disclosed herein can be used to bond the two surfaces temporarily so as to allow the body to heal. Alternatively, adhesion can be undesirable, as may be the case internally after, for example, abdominal surgery (i.e., between loops of the small or large intestine, etc.). In this instance, the compositions disclosed herein can be used to coat one or both opposing surfaces and allowed to cure, thus preventing adhesion, which may be more common at the site of an injury or incision.

As used herein, "soft tissue" refers to connective and supportive tissues in the body including, but not limited to, tendons, ligaments, and other fibrous tissues, fat, blood vessels, muscle, and the like. In one aspect, the compositions disclosed herein can be used for soft tissue repair. "Soft tissue scaffolds" are artificial materials or natural materials with mechanical properties similar to the tissue they are intended to replace or repair, that can provide a base for the formation of new, viable tissue in a subject. In one aspect, the compositions disclosed herein can be used to adhere soft tissue scaffolds to soft tissue.

References in the specification and concluding claims to parts by weight, of a particular element or component in a composition or article, denote the weight relationship between the element or component and any other elements or components in the composition or article for which a part by weight is expressed. Thus, in a composition containing 2 parts by weight of component X and 5 parts by weight of component Y, X and Y are present at a weight ratio of 2:5, and are present in such ratio regardless of whether additional components are contained in the composition.

A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the individual range. Thus, included in this numerical range are individual values such as 2, 3, and 4, sub-ranges such as from 1-3, from 2-4, from 3-5, etc., as well as 1, 2, 3, 4, and 5, individually. The same principle applies to ranges reciting only one numerical value as a minimum or maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, each is specifically contemplated and described herein. For example, if a class of radiopaque agents A, B, and C are disclosed, as well as a class of cyanoacrylate monomers D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered disclosed from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered disclosed from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

I. Radiopaque Agent

The compositions disclosed herein include a radiopaque agent. The radiopaque agent is soluble and stable in cyanoacrylates. The radiopaque agent contains a high density of iodine to facilitate visualization via X-ray.

In one aspect, the radiopaque agent is an iodo compound having one or more ester groups. In another aspect, the radiopaque agent is a compound having at least one aryl group substituted with at least one iodo group and at least one ester group.

In a further aspect, the radiopaque agent includes at least one group having the structure I:

wherein $R^1$ is an alkyl group, an aralkyl group, an iodo-substituted alkyl group, an iodo-substituted aralkyl group, an iodo-substituted aryl group, or a carboxyalkyl group. In another aspect, the radiopaque agent includes two groups having the structure I.

Figure 1:
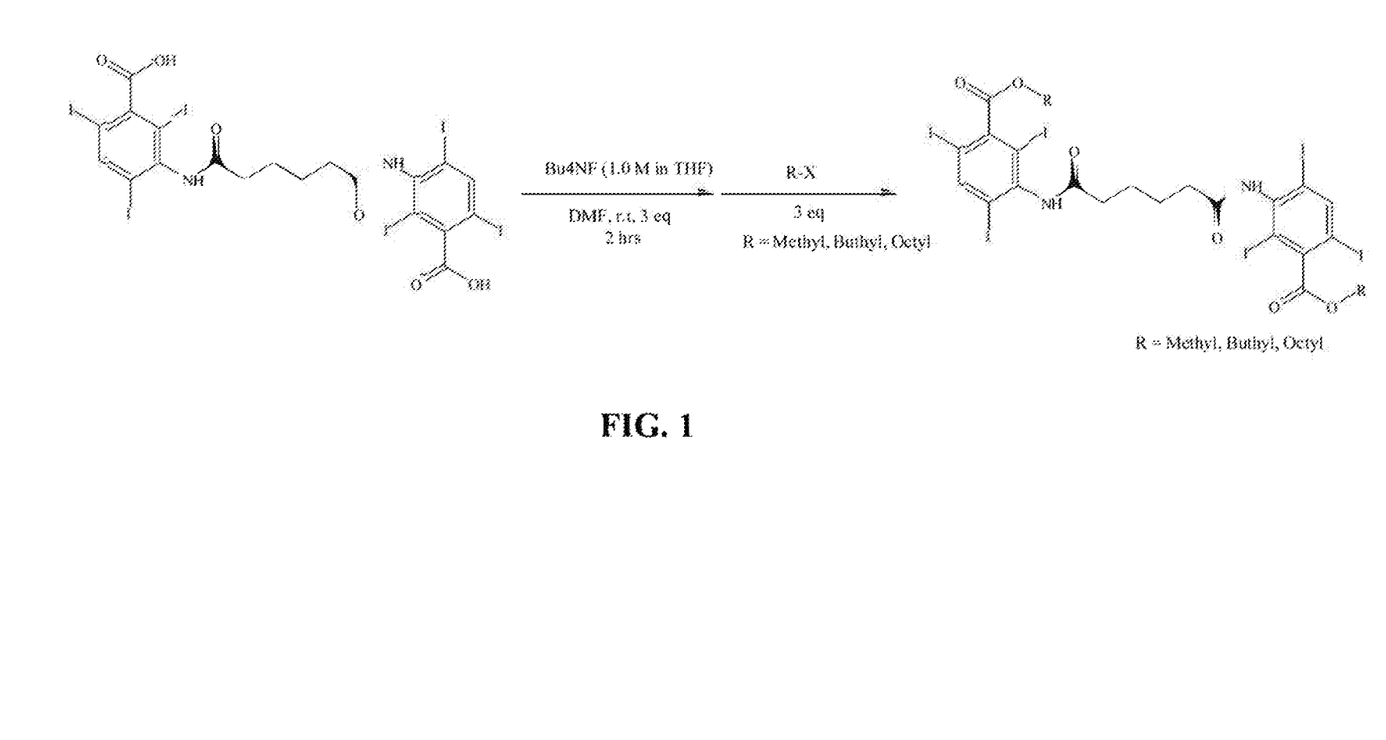
FIG. 1 shows a typical reaction scheme to produce a radiopaque agent.

In one aspect, iodipamide or a related molecule is chemically-modified to produce a diester. For example, an alkyl halide (e.g., butyl iodide) can act as electrophile and a base can be used to deprotonate the acid groups of iodipamide or a related molecule, which can then act as a nucleophile to displace the halide and form the diester. Still further in this aspect, the choice of base can influence product yield as well as ease of purification. FIG. 1 and the Examples provide an exemplary reaction scheme for producing a diester of iodipamide.

In another aspect, the radiopaque agent has the structure II:

wherein $R^1$ is an alkyl group, an aralkyl group, an iodo-substituted alkyl group, an iodo-substituted aralkyl group, an iodo-substituted aryl group, or a carboxyalkyl group. In a further aspect, $R^1$ and $R^2$ are the same alkyl group. In another aspect, $R^1$ and $R^2$ are each a $C_1$ to $C_{18}$ alkyl group, or are a methyl, ethyl, propyl, butyl, pentyl, hexyl, heptyl, or octyl group.

In one aspect, the radiopaque agent is from 5 wt % to 40 wt % of the compositions described herein, or is from 10 wt % to 20 wt % of the compositions described herein, or is about 5, 10, 15, 20, 25, 30, 35, or 40 wt % of the composition, where any value can be a lower and upper end-point of a range (e.g., 5 wt % to 30 wt %, 10 wt % to 20 wt %, etc.).

II. Cyanoacrylate Monomer

The compositions disclosed herein include a cyanoacrylate monomer. In one aspect, the cyanoacrylate monomer is an alkyl cyanoacrylate monomer, a cycloalkyl cyanoacrylate monomer, an allyl cyanoacrylate monomer, an aryl cyanoacrylate monomer, an aralkyl cyanoacrylate monomer, a carboxy alkyl cyanoacrylate monomer, an iodo-substituted cyanoacrylate monomer, or a combination thereof.

In another aspect, the cyanoacrylate monomer is a $C_1$-$C_{18}$ alkyl cyanoacrylate monomer such as, for example, methyl cyanoacrylate, ethyl cyanoacrylate, or butyl cyanoacrylate monomer. In another aspect, the cyanoacrylate monomer is allyl cyanoacrylate, 8-methoxyethyl-2-cyanoacrylate, 2-ethylhexyl cyanoacrylate, 2-octylcyanoacrylate, 2-phenylethyl cyanoacrylate, cyclohexenyl cyanoacrylate, methyl cyanoacrylate, ethyl cyanoacrylate, butyl cyanoacrylate monomer, isopropyl cyanoacrylate, neopentyl cyanoacrylate, octadecyl cyanoacrylate, propargyl cyanoacrylate, tetrahydrofurfuryl cyanoacrylate, β-ethoxy ethyl cyanoacrylate, β-methoxyethyl cyanoacrylate, or a combination thereof.

In still another aspect, the cyanoacrylate monomer is from 30 wt % to 90 wt % of the compositions described herein, or is from 40 wt % to 60 wt % of the compositions, or is about 30, 35, 40, 45, 50, 55, 60, 65, 70, 75, 80, 85, or 90% of the compositions disclosed herein, where any value can be a lower and upper end-point of a range (e.g., 20 wt % to 80 wt %, 40 wt % to 60 wt %, etc.).

III. Preparation of Compositions Composed of Cyanoacrylate Monomers and Radiopaque Agents Provided herein are compositions composed a cyanoacrylate monomer and a radiopaque agent with one or more optional components as discussed below. These compositions are suitable for use in a variety of medical and/or veterinary applications.

In one aspect, the compositions disclosed herein include both a cyanoacrylate monomer and a radiopaque agent having or including the structure of formula I or formula II. In one aspect, the compositions are produced by admixing the cyanoacrylate monomer and the radiopaque agent from 20° C. to 40° C. In a further aspect, the radiopaque agent is has the formula II, where $R^1$ is an alkyl group, an aralkyl group, an iodo-substituted alkyl group, an iodo-substituted aralkyl group, an iodo-substituted aryl group, or a carboxyalkyl group. In another aspect, the cyanoacrylate monomer is butyl cyanoacrylate monomer and $R^1$ and $R^2$ of formula II are the same alkyl group (e.g., methyl, ethyl, propyl, butyl, pentyl, hexyl, heptyl, or octyl groups).

In one aspect, the compositions disclosed herein can be sterilized prior to storage and/or use. Sterilization is desirable to prevent bacterial growth, which can be especially important in compositions designed to have a long shelf life.

In one aspect, sterilization can be carried out by gamma irradiation. One or more stabilizers can be included in the compositions.

In another aspect, sterilization can be carried out in a sealed container at elevated temperature (i.e., at least 110, 115, 120, 125, 130, 135, 140, 145, 150, 155, 160, 165, or 170° C.). In one aspect, sterilization is carried out at 125° C. In another aspect, the container can be glass. In another aspect, the container is made from aluminum, tin, stainless steel, or another metal. In one aspect, the container is an ampoule, vial, metal tube, breakable tube, pouch, or another form. In some aspects, the containers can include components such as caps, seals, linings, O-rings, or the like, made of silicone, TEFLON®, or autoclave-safe plastic.

In another aspect, the amount of time required for sterilization is related to the sterilization temperature used; i.e., lower sterilization temperatures may require longer heating times than higher sterilization temperatures. In one aspect, sterilization at elevated temperature can be carried out for about 0.5, 1, 1.5, 2, 2.5, 3, 3.5, 4, 4.5, 5, 5.5, 6, 6.5, 7, 7.5, 8, 8.5, 9, 9.5, or 10 hours.

In another aspect, sterilization can be accomplished using an electron beam (E-beam) or microwave irradiation. In yet another aspect, sterilization can be accomplished using ultrafiltration or exposure to visible or ultraviolet light, or by exposing the composition to ethylene oxide.

In another aspect, following sterilization, the compositions remain flowable and in a liquid state at room temperature. In a further aspect, sterilization results in population death for bacteria, fungi, archaea, protozoa, viruses, and/or algae, as well as inactivation of bacterial spores.

In any of the above aspects, sterilization does not result in curing of the compositions. Rather, curing occurs during or after administration to a subject.

In one aspect, the compositions disclosed herein exhibit a shelf life of up to a year or more at room temperature, or about 1, 2, 3, 4, 5, 6, 7, 8, 9, 10, 11, 12, 13, 14, or 15 months, where any value can be a lower and upper end-point of a range (e.g., 1 month to 15 months, 8 months to 12 months, etc.). Further in this aspect, even when stored for a minimum of 9 months, the compositions are still radiopaque upon visualization, with a level of intensity comparable to that of commercial products and of newly-prepared samples In another aspect, sterilization as discussed previously can help to extend the shelf life and stability of the products by inhibiting the growth of microbes in the compositions.

In another aspect, the composition has a viscosity of from 1 cP to 5,000 cP, or from about 20 cP to about 1000 cP, or of 1, 5, 10, 15, 20, 25, 50, 100, 150, 200, 250, 300, 350, 400, 450, 500, 550, 600, 650, 700, 750, 800, 850, 900, 950, 1000, 1100, 1200, 1300, 1400, 1500, 2000, or 2500 cP, where any value can be a lower and upper end-point of a range (e.g., 10 cP to 2,000 cP, 20 cP to 1,000 cP, etc.). Here, the compositions have a suitable viscosity so that they can be readily administered (e.g., injected) to a subject In addition to the cyanoacrylate monomer and a radiopaque agent, one or more additional components can be used to produce the compositions described herein.

A. Viscosity Modifier

In some aspects, the compositions further include a viscosity modifier. As used herein, a "viscosity modifier" is a substance, that when added to the compositions disclosed herein, alters the viscosity of the compositions. In one aspect, the viscosity modifier decreases the viscosity of the compositions disclosed herein. In another aspect, the viscosity modifier increases the viscosity of the compositions disclosed herein. In a still further aspect, the viscosity modifier allows the compositions to flow freely at physiological temperature (i.e., 37° C. for humans) for the purpose of injection into or application to a subject in a medical setting.

A viscosity modifier as used herein can be a polymer or can be a small molecule. In one aspect, the viscosity modifier is non-toxic. In another aspect, the viscosity modifier is soluble in the cyanoacrylate monomer. In still another aspect, the viscosity modifier does not accumulate in the tissues of the subject(s) to whom it is applied. In yet another aspect, the presence of a viscosity modifier keeps the compositions from spreading to areas adjacent to the site of application, where treatment may not be desired.

In one aspect, the viscosity modifier can be ethyl myristate, ethyl stearate, ethyl oleate, tri-butyl citrate (TBC), tri-butyl-O-acetyl citrate (TBAC), dibutyl sebacate, a polycaprolactone, a polyglycolide, a polylactide, a polyethylene glycol ether, polyvinylacetate, a polycyanoacrylate, or any combination thereof.

In one aspect, the viscosity modifier is less than 50 wt % of the composition, or is about 5, 10, 15, 20, 25, 30, 35, 40, 45, or 50 wt % of the composition, where any value can be a lower and upper end-point of a range (e.g., 25 wt % to 45 wt %, 30 wt % to 40 wt %, etc.). In certain aspects, the viscosity modifier acts as a thickening agent.

B. Cure Speed Modifier

In some aspects, the compositions disclosed herein include a cure speed modifier. A "cure speed modifier," as used herein, is any compound that alters the curing speed of the cyanoacrylate monomer. A cure speed modifier may decrease the amount of time required for a cyanoacrylate monomer to cure, for example, in order to rapidly stop bleeding from a wound. Alternatively, a cure speed modifier may increase the amount of time required for a cyanoacrylate monomer to cure, thus ensuring that a medical or veterinary practitioner has adequate time to apply the compositions to complex fractures, wounds, etc., while bonding only surfaces where such bonding is desired.

In one aspect, the cure speed modifier can be sulfur dioxide, a sulfonic acid, sulfuric acid, sulfur trioxide, a phosphorous acid, a carboxylic acid, picric acid, boron trifluoride, a $BF_3$-ether complex, $BF_3 \cdot H_2O$, hydrofluoric acid, tin (IV) chloride, iron (III) chloride, nitrogen oxide, boron oxide, phosphoric acid, benzoic acid, cyanoacetic acid, trifluoroacetic acid, tribromoacetic acid, trichloroacetic acid, perchloric acid, hydrochloric acid, hydrobromic acid, fluorosulfonic acid, chlorosulfonic acid, toluenesulfonic acid, $BH_3$, $BCl_3$, $BBr_3$, $AlH_3$, $AlCl_3$, $Al(CH_3)_3$, $B(CH_3)_3$, $Be(CH_3)_2$, formic acid, acetic acid, propionic acid, butyric acid, valeric acid, caproic acid, enanthic acid, caprylic acid, pelargonic acid, capric acid, lauric acid, myristic acid, palmitic acid, stearic acid, arachidic acid, palmitoleic acid, oleic acid, linoleic acid, linolenic acid, arachidonic acid, glyoxylic acid, glycolic acid, acrylic acid, propiolic acid, malonic acid, tartronic acid, mesoxalic acid, dihydroxymalonic acid, lactic acid, hydracrylic acid, glyceric acid, glycidic acid, isobutyric acid, acetoacetic acid, fumaric acid, maleic acid, oxaloacetic acid, tartric acid, crotonic acid, adipic acid, citric acid, aconitic acid, isocitric acid, sorbic acid, benzoic acid, salicylic acid, or any combination thereof. In another aspect, the cure speed modifier is a crown ether such as, for example, 18-crown-6, a podand, a polyalkylene oxide, or a calixarene.

In a further aspect, the cure speed modifier is less than 15,000 ppm of the compositions disclosed herein. In a still further aspect, the cure speed modifier is about 50, 100, 250, 500, 750, 1000, 1250, 1500, 1750, 2000, 2500, 3000, 4000, or 5000 ppm of the composition, where any value can be a lower and upper end-point of a range (e.g., 50 ppm to 5,000 ppm, 100 ppm to 2,500 ppm, etc.).

In one aspect, the cure speed modifier can also act as a stabilizer for the compositions during sterilization by gamma irradiation or another method.

In one aspect, the compositions include both a viscosity modifier and a cure speed modifier.

IV. Applications of the Radiopaque Cyanoacrylate Compositions

The compositions described herein have numerous medical applications. The compositions are fluids and are readily injectable using equipment known in the art (e.g., via a narrow gauge device, syringe, catheter, needle, cannula, or tubing). Upon administration to the subject, the compositions form an insoluble solid upon administration to the subject.

In one aspect, provided herein is a method for reducing or inhibiting blood flow in a blood vessel of a subject comprising introducing into the vessel the compositions described herein, wherein the composition creates an artificial embolus within the vessel. Further in this aspect, the method reduces or inhibits blood flow to a tumor, an aneurysm, a varicose vein, an arteriovenous malformation, or a bleeding wound.

In another aspect, provided herein is a method for reinforcing the inner wall of a blood vessel wherein the compositions disclosed herein are introduced into the vessel. The composition can be introduced into the vessel in a sufficient amount to coat the inner lining of the vessel so that the vessel is not blocked. For example, the compositions can be injected into a vessel where there is an aneurysm and can thus reduce the likelihood of or prevent the rupture of the aneurysm.

In yet another aspect, provided herein is a method for closing or sealing a puncture in a blood vessel in a subject wherein the compositions disclosed herein are applied to the puncture. Further in this aspect, the compositions can be injected into a vessel in a sufficient amount to close or seal the puncture from within the vessel so that the vessel is not blocked. In another embodiment, the compositions can be applied to the puncture on the exterior surface of the vessel to seal the puncture.

In still another aspect, provided herein is a method for repairing a bone fracture in a subject wherein the fractured bone is contacted with compositions disclosed herein. In an alternative aspect, provided herein is a method for adhering a substrate to a bone of a subject wherein (1) the bone and/or substrate are first contacted with the compositions disclosed herein and (2) the substrate is applied to the bone to adhere the substrate to the bone. Examples of fractures include, but are not limited to, a complete fracture, an incomplete fracture, a linear fracture, a transverse fracture, an olique fracture, a compression fracture, a spiral fracture, a comminuted fracture, a compacted fracture, or an open fracture. The compositions disclosed herein may aid in the maintenance or the reduction of such fractures, allow less invasive surgery, reduce operating room time, reduce costs, and provide a better outcome by reducing the risk of post-traumatic arthritis.

In other aspects, the compositions disclosed herein can be used to join small fragments of highly comminuted fractures. In this aspect, small pieces of fractured bone can be adhered to an existing bone. It is especially challenging to maintain reduction of the small fragments by drilling them with mechanical fixators. The smaller and greater the number of fragments, the greater the problem. In one aspect, the compositions disclosed herein may be injected in small volumes to crate spot welds as described above in order to fix the fracture rather than filling the entire crack. The small biocompatible spot welds would minimize interference with healing of the surrounding tissue and would not necessarily have to be biodegradable. In this respect, it would be similar to permanently implanted hardware.

In other aspects, the compositions disclosed herein can adhere a substrate to bone or related tissues such as, for example, cartilage, ligaments, tendons, and the like. For example, implants made from titanium oxide, stainless steel, or other metals are commonly used to repair fractured bones. The compositions can be applied to the metal substrate, the bone, or both, prior to adhering the substrate to the bone. In other aspects, the substrate can be a fabric (e.g., an internal bandage), a tissue graft, a patch, or a wound healing material. Thus in addition to bonding bone fragments, the compositions disclosed herein can facilitate the bonding of substrate to bone, which can facilitate bone repair and recovery.

The compositions disclosed herein have numerous dental applications. For example, they can be used to seal breaks or cracks in teeth, for securing crowns, for securing allografts, and for seating implants and dentures. The composition can be applied to specific points in the mouth followed by attaching the implant to the substrate and subsequent curing.

In one aspect, provided herein is a method for bonding a soft tissue scaffold to soft tissue, or two soft tissue scaffolds to two soft tissues wherein (1) the compositions disclosed herein are applied to the tissue scaffold(s) and/or soft tissue(s) and (2) the soft tissue is contacted with the soft tissue scaffold or the two soft tissues are contacted with the two soft tissue scaffolds.

The compositions disclosed herein can be used to position biological scaffolds in a subject. Small adhesive tacks composed of the compositions would not interfere with migration of cells or transport of small molecules into or out of the scaffold.

In a further aspect, provided herein is a method for treating a wound in a subject wherein the compositions disclosed herein are applied to the wound. In another aspect, provided herein is a method for closing or sealing a puncture in an internal tissue or membrane wherein (1) the compositions disclosed herein are applied to a patch and/or the puncture and (2) the patch is adhered to the puncture.

In yet another aspect, provided herein is a method for filling a tissue void in a subject wherein the compositions disclosed herein are introduced into the void. In an alternative aspect, provided herein is a method for sealing a fistula in a subject wherein the fistula is contacted or filled with the compositions disclosed herein. In still another aspect, the compositions can be used to close or seal a puncture in an internal tissue or a membrane.

In still another aspect, provided herein is a method for preventing or reducing the adhesion of two tissues in a subject, wherein at least one surface of one of the tissues is contacted with the compositions disclosed herein.

It is also contemplated that the compositions disclosed herein can encapsulate, scaffold, seal, or hold one or more bioactive agents. The bioactive agents can be any drug including, but not limited to, antibiotics, pain relievers, immune modulators, growth factors, enzyme inhibitors, hormones, mediators, messenger molecules, cell signaling molecules, receptor agonists, oncolytics, chemotherapy agents, or receptor antagonists.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures, and other reaction ranges and conditions that can be used to optimize the product purity and yield obtained from the described process. Only reasonable and routine experimentation will be required to optimize such process conditions.

Example 1: Synthesis of Radiopaque Diesters

A typical synthetic protocol for synthesis of a radiopaque diester was as follows: 1.0 M Bu$_4$NF in tetrahydrofuran was added to a solution of iodipamide in dimethylformamide at room temperature. The mixture was stirred for 2 hours, then alkyl halide was added to the reaction mixture. Stirring continued at room temperature until the reaction was completed, typically in 2-3 days. After completion of the reaction, deionized water was added to the reaction mixture to cause the product to precipitate as a glumerous or gel-like material, which was further purified by recrystallization.

Yields were approximately 80% after isolation of the product. A typical reaction scheme is shown in FIG. 1.

Example 2: Radiopacity and Stability of Radiopaque Diesters

Purified radiopaque diesters prepared according to the procedure described in Example 1 were formulated to 15 wt % in a 3:2 (weight ratio) mixture of n-butyl cyanoacrylate monomer:ethyl myristate. The formulation was prepared by adding sequentially to n-butyl cyanoacrylate monomer, the radiopaque diester, ethyl myristate, and acetic Acid (800 ppm) followed by stirring overnight at room temperature. Five formulations were tested for radiopacity; these are presented in Table 1:

TABLE 1

Formulations Tested for Radiopacity/Stability

| Sample Code | Radiopaque Reagent | Amount | Notes |
|---|---|---|---|
| 1 | Diethyl iodipamide ester | 20 g | Not sterilized |
| 2 | Dibutyl iodipamide ester | 20 g | Not sterilized |
| 3 | Dibutyl iodipamide ester | 20 g | Sterilized |
| 4 | Dibutyl iodipamide ester | 17 g | Sterilized, 9 months old |
| 5 | Dioctyl iodipamide ester | 20 g | Not sterilized |

Figure 2:
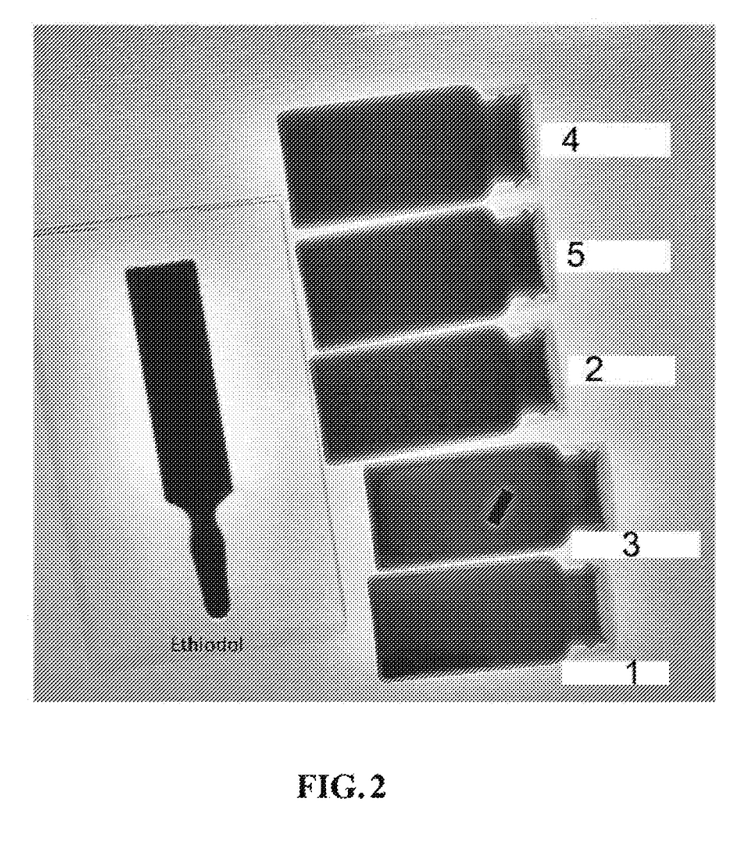
FIG. 2 shows radiopacity of compositions according to the present invention after various sterilization and/or storage conditions. Left side: ETHIODOL® commercial product (ethiodized poppy oil only) for comparison. Right side: (1) sterilized, 9-month-old dibutyl iodipamide ester (17 g); (2) non-sterilized dioctyl iodipamide ester (20 g); (3) non-sterilized dibutyl iodipamide ester (20 g); (4) sterilized dibutyl iodipamide ester (20 g); and (5) non-sterilized diethyl iodipamide ester (20 g).

Radiopacity of the various samples can be seen in FIG. 2 as compared to an ETHIODOL® sample. As pictured, the ETHIODOL® reference is an unmixed vial, which would typically be used in a 2:3 ratio of ETHIODOL®:n-butyl cyanoacrylate monomer, and the diester intensity of this reference under X-ray would be approximately equal to the experimental samples.

All formulations demonstrated sufficient radiopacity for the purpose of differentiation under X-ray radiation.

When sterilization was performed, the present formulations were heated to 125° C. Under accelerated aging conditions, shelf life of the formulations was found to be at least one year.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A composition comprising a cyanoacrylate monomer and a radiopaque agent comprising at least one group comprising the structure II wherein $R^1$ and $R^2$ are each a $C_4$ to $C_{18}$ alkyl group.

2. The composition of claim 1, wherein $R^1$ and $R^2$ are the same alkyl group.

3. The composition of claim 1, wherein $R^1$ and $R^2$ are each butyl, pentyl, hexyl, heptyl, or octyl.

4. The composition of claim 1, wherein the cyanoacrylate monomer is an alkyl cyanoacrylate monomer, a cycloalkyl cyanoacrylate monomer, an allyl cyanoacrylate monomer, an aryl cyanoacrylate monomer, an aralkyl cyanoacrylate monomer, a carboxy alkyl cyanoacrylate monomer or an iodo-substituted cyanoacrylate monomer.

5. The composition of claim 1, wherein the cyanoacrylate monomer is a $C_1$-$C_{18}$ alkyl cyanoacrylate monomer.

6. The composition of claim 1, wherein the alkyl cyanoacrylate monomer is butyl cyanoacrylate monomer.

7. The composition of claim 1, wherein the cyanoacrylate monomer is butyl cyanoacrylate monomer and $R^1$ and $R^2$ are the same alkyl group.

8. The composition of claim 7, wherein $R^1$ and $R^2$ are each butyl, pentyl, heptyl, or octyl.

9. The composition of claim 1, wherein the cyanoacrylate monomer is from 30 wt % to 90 wt % of the composition.

10. The composition of claim 1, wherein the radiopaque agent is from 5 wt % to 40 wt % of the composition.

11. The composition of claim 1, wherein the composition further comprises a viscosity modifier.

12. The composition of claim 11, wherein the viscosity modifier comprises ethyl myristate, ethyl stearate, ethyl oleate, tri-butyl citrate (TBC), tri-butyl-O-acetyl citrate (TBAC), dibutyl sebacate, a polycaprolactone, a polyglycolide, a polylactide, a polyethylene glycol ether, polyvinyl acetate, or any combination thereof.

13. The composition of claim 11, wherein the viscosity modifier is less than 50 wt % of the composition.

14. The composition of claim 1, wherein the composition further comprises a cure speed modifier.

15. The composition of claim 14, wherein the cure speed modifier comprises sulfur dioxide, a sulfonic acid, sulfuric acid, sulfur trioxide, a phosphorous acid, a carboxylic acid, picric acid, boron trifluoride, a $BF_3$-ether complex, $BF_3 \cdot H_2O$, hydrofluoric acid, tin (IV) chloride, iron (III) chloride, nitrogen oxide, boron oxide, phosphoric acid, benzoic acid, cyanoacetic acid, trifluoroacetic acid, tribromoacetic acid, trichloroacetic acid, perchloric acid, hydrochloric acid, hydrobromic acid, fluorosulfonic acid, chlorosulfonic acid, toluenesulfonic acid, $BH_3$, $BCl_3$, $BBr_3$, $AlH_3$, $AlCl_3$, $Al(CH_3)_3$, $B(CH_3)_3$, $Be(CH_3)_2$, formic acid, acetic acid, propionic acid, butyric acid, valeric acid, caproic acid, enanthic acid, caprylic acid, pelargonic acid, capric acid, lauric acid, myristic acid, palmitic acid, stearic acid, arachidic acid, palmitoleic acid, oleic acid, linoleic acid, linolenic acid, arachidonic acid, glyoxylic acid, glycolic acid, acrylic acid, propiolic acid, malonic acid, tartronic acid, mesoxalic acid, dihydroxymalonic acid, lactic acid, hydracrylic acid, glyceric acid, glycidic acid, isobutyric acid, acetoacetic acid, fumaric acid, maleic acid, oxaloacetic acid, tartric acid, crotonic acid, adipic acid, citric acid, aconitic acid, isocitric acid, sorbic acid, benzoic acid, salicylic acid, a crown ether, a podand, a polyalkylene oxide, a calixarene, or any combination thereof.

16. The composition of claim 14, wherein the cure speed modifier comprises acetic acid or citric acid.

17. The composition of claim 14, wherein the cure speed modifier is less than 15,000 ppm of the composition.

18. The composition of claim 1, wherein the composition has a viscosity of from 1 cP to 5,000 cP.

19. The composition of claim 1, wherein the composition is sterilized.

20. A method for reducing or inhibiting blood flow in a blood vessel of a subject comprising introducing into the vessel the composition of claim 1, wherein the composition creates an artificial embolus within the vessel.

21. The method of claim 20, wherein the method reduces or inhibits blood flow to a tumor, an aneurysm, a varicose vein, an arteriovenous malformation, or a bleeding wound.

22. A method for reinforcing the inner wall of a blood vessel in a subject comprising introducing into the vessel the composition of claim 1.

23. A method for closing or sealing a puncture in a blood vessel in a subject comprising applying to the puncture the composition of claim 1.

24. A method for repairing a bone fracture in a subject comprising contacting the fractured bone with the composition of claim 1.

25. A method for adhering a substrate to a bone of a subject comprising (1) contacting the bone and/or substrate with the composition of claim 1 and (2) applying the substrate to the bone to adhere the substrate to the bone.

26. A method for adhering a bone-tissue scaffold to a bone of a subject comprising contacting the bone and/or bone-tissue scaffold with the composition of claim 1 and (2) applying the bone-tissue scaffold to the bone to adhere the bone-tissue scaffold to the bone.

27. A method for bonding a soft tissue scaffold to soft tissue or two soft tissue scaffolds or two soft tissues comprising (1) applying to the tissue scaffolds and/or soft tissues the composition of claim 1 and (2) contacting the soft tissue scaffold to soft tissue, the two soft tissue scaffolds or the two soft tissues.

28. A method for treating a wound within a subject comprising applying to the wound the composition of claim 1.

29. A method for closing or sealing a puncture in internal tissue or membrane comprising (1) applying the composition of claim 1 to a patch and/or the puncture and (2) adhering the patch to the puncture.

30. A method for filling a tissue void in a subject comprising introducing into the void the composition of claim 1.

31. A method for sealing a fistula in a subject, the method comprising contacting or filling the fistula with the composition of claim 1.

32. A method for preventing or reducing adhesion of two tissues in a subject having a wound of surgical incision comprising contacting at least one surface of the tissue with the composition of claim 1.

33. A method for sealing breaks or cracks in teeth comprising contacting the breaks or cracks with the composition of claim 1.

34. A method for securing crowns or dental implants comprising (1) contacting the crown with the composition of claim 1, and (2) placing the crown or dental implant in the mouth of a subject.

35. The composition of claim 1, further comprising one or more bioactive agents.

36. The composition of claim 35, wherein the one or more bioactive agents comprise an antibiotics, a pain reliever, an immune modulator, a growth factor, an enzyme inhibitor, a hormone, a mediator, a messenger molecule, cell a signaling molecule, a receptor agonist, an oncolytic, a chemotherapy agent, a receptor antagonist, or a combination thereof.

37. A composition produced by admixing a cyanoacrylate monomer and a radiopaque agent and a radiopaque agent comprising at least one group comprising the structure II

II wherein $R^1$ and $R^2$ are each a $C_4$ to $C_{18}$ alkyl group.

* * * * *